United States Patent [19]  
Kulmburg

[11] Patent Number: 5,039,574  
[45] Date of Patent: Aug. 13, 1991

[54] DENTAL PROSTHESIS WITH COBALT ALLOY FRAME

[75] Inventor: Alfred Kulmburg, Kapfenberg, Austria

[73] Assignee: Vereinigte Edelstahlwerke AG, Vienna, Austria

[21] Appl. No.: 96,199

[22] Filed: Sep. 14, 1987

Related U.S. Application Data

[63] Continuation of Ser. No. 810,326, Nov. 25, 1985, abandoned.

[30] Foreign Application Priority Data

Apr. 6, 1984 [AT] Austria .................................. 1167/84

[51] Int. Cl.[5] .............................................. A61C 13/01
[52] U.S. Cl. ..................................... 428/433; 428/469; 433/207; 420/436; 420/440
[58] Field of Search ................. 420/436, 440; 433/207; 428/433, 469, 472

[56] References Cited

U.S. PATENT DOCUMENTS 3,177,074 4/1965 Luce et al. ........................... 420/440
4,263,045 4/1981 Prosen ................................. 420/440

FOREIGN PATENT DOCUMENTS 0259880 2/1968 Austria .
0041938 12/1981 European Pat. Off. .
0579635 7/1976 Switzerland .
1264587 2/1972 United Kingdom .

Primary Examiner—R. Dean  
Assistant Examiner—Margery S. Phipps  
Attorney, Agent, or Firm—Sandler, Greenblum & Bernstein

[57] ABSTRACT

The invention concerns a ceramically coated dental prosthesis in which the metal frame comprises an alloy containing, each in percent by weight: 0 to 0.4 carbon, 0.1 to 5.0 silicon, 0.01 to 8.0 manganese, 25 to 35 chromium, 1.0 to 8.0 molybdenum, 0.1 to 5 niobium, 0 to 0.3 nickel, 0 to 1.0 iron, the remainder being cobalt and impurities resulting from manufacturing conditions.

8 Claims, No Drawings

DENTAL PROSTHESIS WITH COBALT ALLOY FRAME

CROSS-REFERENCE TO RELATED APPLICATION

This application is a continuation application of our copending United States PCT application Serial No. 06/810,326, and entitled "DENTAL ALLOY".

BACKGROUND OF THE INVENTION

The present invention relates to a new and improved dental prosthesis.

In its more particular aspects the present invention specifically relates to a new and improved dental prosthesis which constitutes a ceramically coated dental prosthesis containing a metal frame and dental ceramic material. Such dental prosthesis may constitute a coated crown, a bridge or the like.

It is a basic prerequisite for alloys which are intended for use in the human body that such alloys must be physiologically safe. Besides the fact which is obvious as such, that the alloy must not dissolve in the human body, a number of further requirements exist when using such alloys in the oral cavity. With respect to the very high corrosive stresses, for example, extreme fluctuations of the pH-value in the oral cavity accompanied by simultaneously variable concentrations of corrosion promoting ions, for example, chloride ions, these alloys still additionally must have properties which are of importance in the course of manufacturing dental prostheses, bridges, or the like. For reasons of appearance as well as of durability, dental prostheses are coated with a ceramic material and this ceramic material is applied to the metal surface by means of firing processes. When firing the ceramic material it must be considered that the temperature is raised by approximately 1,000° C. and, therefore, the differences in the thermal coefficients of expansion may not be too great. Furthermore, if such differences do exist, the thermal expansion of the alloy component must be smaller than that of the ceramic component, so that the ceramic portion is not subjected to tensile stress but to compressive stress after cooling of the dental prostheses because ceramic material possesses only low tensile strength, however, high compressive strength.

Further there often exists the desire that the ceramic material should be applied not by means of a single firing process but by means of a number of firing processes and the behavior during these individual firing processes should correspond to the behavior as initially explained.

SUMMARY OF THE INVENTION

Therefore, with the foregoing in mind it is a primary object of the present invention to provide a new and improved dental prosthesis containing a metal frame having a linear thermal expansion coefficient which is unaffected by multiple firing processes required for preparing the dental prosthesis.

Now in order to implement this and still further objects of the invention which will become more readily apparent as the description proceeds, the dental prosthesis of the present development is manifested by the features that the metal frame comprises an alloy containing, each in percent by weight: carbon 0 to 0.4, preferably, 0.05 to 0.3, silicon 0.1 to 5.0, preferably 0.1 to 3.0, manganese 0.01 to 8.0, preferably 0.3 to 3.0, chromium 25 to 35, preferably 27 to 33, molybdenum 1.0 to 8.0, preferably 4 to 7, niobium 0.1 to 5, preferably 0.5 to 3, nickel 0 to 0.3, iron 0 to 1.0 and, if desired, copper 0.1 to 5.0, preferably 0.5 to 2.0, the remainder being cobalt and impurities resulting from manufacturing conditions.

An alloy having the inventive composition possesses the coefficient of expansion desired for dental frames to be coated with a ceramic material. At the same time the required mechanical values, especially with respect to elongation of fracture and hardness are also satisfied. However, it turned out completely surprising that this alloy possesses high dimensional stability even after exposed to a plural number of thermal loads. These high thermal loads not only occur during the plural firings of the ceramic layer but also are caused by the fitting operation of the prosthesis, for instance, to the counter-denture. During such fitting operation the dentist carries out an adaptation to the counter-denture by mechanically removing the ceramic layer, whereby extreme local thermal loads can arise. If then an irreversible dimensional alteration takes place, this can result in premature destruction of the ceramic material, or in an ugly discoloration of the ceramic material, for example, due to the formation of hair cracks and the penetration of coloring matter.

DETAILED DESCRIPTION OF THE PREFERRED EMBODIMENTS

In the following the invention is further explained with reference to Examples.

EXAMPLES

During the firing of ceramic materials containing, for instance, 80% by weight of feldspar, 18% by weight of quartz and 2% by weight of boron frit, onto the frame to be coated, the sample is heated one or more times to temperatures between 950° C. and 1,000° C. Heating is generally for 10 minutes with intermediate cooling to room temperature in order to apply, for example, the mass to be fired. For simulating a triple firing and at the same time determining dimensional alterations, different test bodies having a-composition in accordance with the following Table and a diameter of 10 mm and a height of 10 mm, were first heated to 1,000° C. in vacuo, maintained at this temperature for 10 minutes and then rapidly cooled to room temperature. This procedure was repeated three times. No alterations in the diameter as well as in the height could be determined after the first, the second as well as the third firing.

As can be seen from the Table, the coefficient of thermal expansion is in the range between $13.7 \times 10^{-6}$ °C.$^{-1}$ and $15.5 \times 10^{-6}$ °C.$^{-1}$, and thus lies within the desired limits for the thermal expansion in order to maintain the ceramic material to be applied under a desired compressive stress and not under a tensile stress. The hardness between 290 and 410 HV10 also corresponds to the requirements and therefore the proof stress and elongation of fracture permit mechanical processing in correspondence therewith.

| | CHEMICAL COMPOSITION | | | | | | | | PROPERTIES | | | |
|---|---|---|---|---|---|---|---|---|---|---|---|---|
| | | | | | | | | | Hardness | Proof Stress Rp 0.2 | Elongation of Fracture | Coeff. of Expansion 20°-500° C. |
| | C | Si | Mn | Cr | Mo | Ni | Cu | Nb | Co | NV10 | N/mm² | % | $10^{-6°}$ C.$^{-1}$ |
| 1 | 0.25 | 0.45 | 0.52 | 26.52 | 3.81 | 0.12 | 0.12 | 0.20 | Rem | 330 | 600 | 9 | 15.0 |
| 2 | 0.38 | 0.64 | 6.80 | 31.12 | 5.12 | 0.16 | 0.32 | 0.12 | Rem | 300 | 585 | 10 | 13.7 |
| 3 | 0.12 | 0.52 | 0.05 | 30.21 | 5.46 | 0.08 | 0.57 | 1.02 | Rem | 315 | 580 | 9 | 14.5 |
| 4 | 0.02 | 0.61 | 0.18 | 32.12 | 4.96 | 0.05 | 0.28 | 3.80 | Rem | 290 | 560 | 11 | 14.8 |
| 5 | 0.37 | 0.43 | 0.12 | 30.32 | 5.38 | 0.09 | 0.12 | 0.32 | Rem | 335 | 610 | 8 | 14.8 |
| 6 | 0.39 | 2.80 | 0.20 | 29.82 | 5.08 | 0.11 | 0.50 | 0.21 | Rem | 410 | 680 | 5 | 15.5 |
| 7 | 0.33 | 0.31 | 0.09 | 28.96 | 5.81 | 0.08 | 4.12 | 0.61 | Rem | 335 | 590 | 8 | 14.8 |
| 8 | 0.21 | 1.06 | 0.51 | 34.79 | 5.27 | 0.07 | 0.23 | 0.16 | Rem | 370 | 630 | 6 | 13.9 |
| 9 | 0.26 | 0.42 | 0.65 | 30.78 | 6.86 | 0.14 | 0.12 | 0.41 | Rem | 340 | 600 | 8 | 15.4 |

While there are described present preferred embodiments of the invention, it is to be distinctly understood that the invention is not limited thereto, but may be otherwise variously embodied and practiced within the scope of the following claims. ACCORDINGLY,

What I claim is:

1. A ceramically coated dental prosthesis comprising: a metal frame;
a coating of ceramic material on said metal frame; and
said metal frame constituting an alloy consisting essentially of, each in percent by weight: 0 to 0.4 carbon, 0.1 to 5.0 silicon, 0.01 to 8.0 manganese, 25 to 35 chromium, 1.0 to 8.0 molybdenum, 0.1 to 5.0 niobium, 0 to 0.3 nickel, 0 to 1.0 iron, the remainder being cobalt and impurities resulting from manufacturing conditions.

2. The ceramically coated dental prosthesis according to claim 1, wherein:
said metal frame possesses 27 to 33% by weight of chromium.

3. The ceramically coated dental prosthesis according to claim 1, wherein:
said metal frame has a coefficient of thermal expansion which is less than the thermal coefficient of expansion of said ceramic material.

4. The ceramically coated dental prosthesis according to claim 1, wherein:
said metal frame has a coefficient of thermal expansion which is substantially unaffected by exposure to a plurality of thermal loads.

5. The ceramically coated dental prosthesis according to claim 1, wherein:
said metal frame has a coefficient of thermal expansion in the range of $13.7 \times 10^{-6°}$ C.$^1$ to $15.5 \times 10^{-6°}$ C.$^{-1}$.

6. The ceramically coated dental prosthesis according to claim 1, wherein:
said metal frame has a hardness value between 290 and 410 HV10.

7. A ceramically coated dental prosthesis comprising: a metal frame;
a coating of ceramic material on said metal frame; and
said metal frame constituting an alloy consisting essentially of, each in percent by weight: 0 to 0.4 carbon, 0.1 to 5.0 silicon, 0.01 to 8.0 manganese, 25 to 35 chromium, 1.0 to 8.0 molybdenum, 0.1 to 5.0 niobium, 0 to 0.3 nickel, 0 to 1.0 iron, 0.1 to 5.0 copper, the remainder being cobalt and impurities resulting from manufacturing conditions.

8. The ceramically coated dental prosthesis according to claim 7, wherein:
said metal frame possesses 27 to 33% by weight of chromium.

* * * * *